United States Patent
Kodama et al.

(10) Patent No.: US 8,106,186 B2
(45) Date of Patent: Jan. 31, 2012

(54) TRANSITION METAL PHOSPHINE COMPLEX, METHOD FOR PRODUCING SAME, AND ANTICANCER AGENT CONTAINING TRANSITION METAL PHOSPINE COMPLEX

(75) Inventors: Hiroaki Kodama, Saga (JP); Keisuke Ohto, Saga (JP); Nobuhiko Oohara, Tokyo (JP); Kazuhiro Nakatsui, Tokyo (JP); Yoshirou Kaneda, Tokyo (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 1139 days.

(21) Appl. No.: 11/911,911

(22) PCT Filed: Apr. 17, 2006

(86) PCT No.: PCT/JP2006/308035
§ 371 (c)(1),
(2), (4) Date: Oct. 18, 2007

(87) PCT Pub. No.: WO2006/112435
PCT Pub. Date: Oct. 26, 2006

(65) Prior Publication Data
US 2009/0076267 A1    Mar. 19, 2009

(30) Foreign Application Priority Data

Apr. 18, 2005 (JP) .................. 2005-119404
Dec. 6, 2005 (JP) .................. 2005-352476

(51) Int. Cl.
*C07B 47/00* (2006.01)
*C07D 487/22* (2006.01)
*A01N 43/36* (2006.01)

(52) U.S. Cl. ........ 540/145; 428/601; 428/608; 424/604; 546/1

(58) Field of Classification Search ............ 514/89; 428/601, 608, 606; 424/604; 546/1; 540/145
See application file for complete search history.

(56) References Cited

U.S. PATENT DOCUMENTS 4,831,170 A    5/1989   Timmer et al.
5,037,812 A    8/1991   Berners-Price et al.
6,159,957 A *  12/2000  Berners-Price et al. ........ 514/89

FOREIGN PATENT DOCUMENTS
EP    0164970 A2    12/1985

OTHER PUBLICATIONS

Pinedo et al, "Translational Research . . . ", The Oncologist 2000; 5(suppl1); 1-2. [www.The Oncologist.com].*
McMahon, G., VEGF Receptor Signaling in Tumor Angiogenisis. The Oncologist 2000;5(suppl 1):3-10. [www.The Oncologist.com].*
International Search Report of PCT/JP2006/308035, date of mailing May 23, 2006.

* cited by examiner

*Primary Examiner* — Paul V. Ward
(74) *Attorney, Agent, or Firm* — Westerman, Hattori, Daniels & Adrian, LLP

(57) ABSTRACT

There is provided a novel transition metal phosphine complex having excellent anticancer activity. The transition metal phosphine complex is represented by general formula (1):

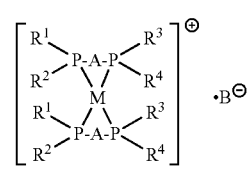

(1)

(wherein $R^1$s and $R^3$s each represent an alkyl group, a cycloalkyl group, an aryl group, an aralkyl group, a pyridyl group, or a pyrimidyl group; $R^2$s and $R^4$s each represent an alkyl group or a cycloalkyl group, provided that each $R^1$ and each $R^2$ are not the same group and that each $R^3$ and each $R^4$ are not the same group; As each represent a linear alkylene group or a cis-vinylene group; M represents a gold atom, a silver atom, a copper atom, or a platinum atom; and B represents an anionic species).

6 Claims, No Drawings

TRANSITION METAL PHOSPHINE COMPLEX, METHOD FOR PRODUCING SAME, AND ANTICANCER AGENT CONTAINING TRANSITION METAL PHOSPINE COMPLEX

TECHNICAL FIELD

The present invention relates to a novel transition metal phosphine complex, a method for producing the transition metal phosphine complex, and an anticancer agent containing the transition metal phosphine complex.

BACKGROUND ART

Platinum complexes, such as cisplatin (cis-diamminedichloroplatinum(II)), carboplatin (cis-1,1-cyclobutanedicarboxylatodiammineplatinum(II), and nedaplatin (cis-O,O'-glycolatodiammineplatinum(II), have strong anticancer activity and are currently used as main anticancer agents.

In general formula:

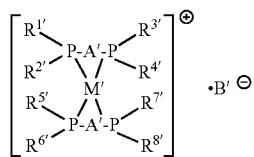

a transition metal phosphine complex (see Patent Document 1) wherein $R^{1'}$ to $R^{8'}$ are the same or different and they each represent a phenyl group, a substituted phenyl group, or a pyridyl group; A?s each represent a linear alkylene group or a cis-vinylene group; M' represents a gold atom, a silver atom, or a copper atom; and B' represents an anionic species, and a transition metal phosphine complex (see Patent Document 2) wherein $R^{1'}$ to $R^{8'}$ are the same and they each represent a phenyl group, a substituted phenyl group, or an ethyl group or wherein $R^{1'}$, $R^{2'}$, $R^{7'}$, and $R^{8'}$ each represent a phenyl group; $R^{3'}$ to $R^{6'}$ each represent an ethyl group; As each represent a linear alkylene group or a cis-vinylene group; M' represents a gold atom, a silver atom, or a copper atom; and B' represents an anionic species, are known to have anticancer activity comparable to that of cisplatin.

Patent Document 1: PCT Japanese Translation Patent Publication No. 10-509957
Patent Document 2: Japanese Unexamined Patent Application Publication No. 61-10594

DISCLOSURE OF INVENTION

Problems to be Solved by the Invention

In general, however, it is known that the anticancer activity and anticancer spectra of compounds depend significantly on chemical structures and that minute structural differences result in big differences in these properties. Furthermore, the effect of an anticancer agent varies from person to person. For example, even taxol, which has been regarded as the best anticancer agent, has a availability of about 30%. Thus, development of various novel anticancer agents having different chemical structures is required.

The present invention has been made in consideration of the above situation. It is an object of the present invention to provide a novel transition metal phosphine complex having excellent anticancer activity, a method for producing the transition metal phosphine complex, and an anticancer agent containing the transition metal phosphine complex.

Means for Solving the Problems

The inventors have conducted intensive studies on a novel transition metal phosphine complex having anticancer activity and have found that a transition metal phosphine complex having a specific structure has excellent anticancer activity. The findings have led to the completion of the present invention.

The present invention provides a transition metal phosphine complex represented by general formula (1):

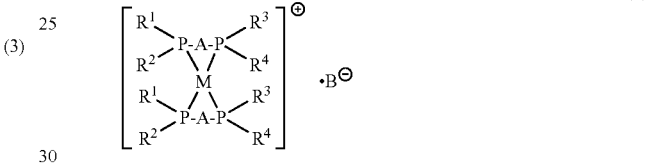

(wherein $R^1$s and $R^3$s each represent an alkyl group, a cycloalkyl group, an aryl group, an aralkyl group, a pyridyl group, or a pyrimidyl group; $R^2$s and $R^4$s each represent an alkyl group or a cycloalkyl group, provided that each $R^1$ and each $R^2$ are not the same group and that each $R^3$ and each $R^4$ are not the same group; As each represent a linear alkylene group or a cis-vinylene group; M represents a gold atom, a silver atom, a copper atom, or a platinum atom; and B represents an anionic species).

The present invention also provides the transition metal phosphine complex in which $R^1$s and $R^3$s each represent a pyridyl group or a pyrimidyl group.

The present invention also provides the transition metal phosphine complex in which M represents a gold atom.

The present invention also provides the transition metal phosphine complex that is bis(1,2-bis(tert-butyl(2-pyridyl)phosphino)ethane)gold(I) chloride, bis(1,2-bis(tert-butyl(2-pyrimidyl)phosphino)ethane)gold(I) chloride, bis(1,2-bis(tert-butyl(methyl)phosphino)ethane)gold(I) chloride, bis(1,2-bis(methyl(phenyl)phosphino)ethane)gold(I) chloride, bis(1,2-bis(tert-butyl(2-pyridyl)phosphino)ethane)gold(I) bromide, bis(1,2-bis(tert-butyl(2-pyrimidyl)phosphino)ethane)gold(I) bromide, bis(1,2-bis(tert-butyl(methyl)phosphino)ethane)gold(I) bromide, bis(1,2-bis(methyl(phenyl)phosphino)ethane)gold(I) bromide, bis(1,2-bis(tert-butyl(2-pyridyl)phosphino)ethane)gold(I) iodide, bis(1,2-bis(tert-butyl(2-pyrimidyl)phosphino)ethane)gold(I) iodide, bis(1,2-bis(tert-butyl(methyl)phosphino)ethane)gold(I) iodide, or bis(1,2-bis(methyl(phenyl)phosphino)ethane)gold(I) iodide.

The present invention provides an optically active form of the transition metal phosphine complex.

The present invention provides a method for producing a transition metal phosphine complex represented by general formula (1):

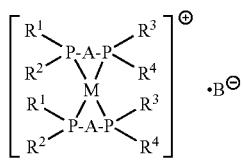
(1)

(wherein R¹s and R³s each represent an alkyl group, a cycloalkyl group, an aryl group, an aralkyl group, a pyridyl group, or a pyrimidyl group; R²s and R⁴s each represent an alkyl group or a cycloalkyl group, provided that each R¹ and each R² are not the same group and that each R³ and each R⁴ are not the same group; As each represent a linear alkylene group or a cis-vinylene group; M represents a gold atom, a silver atom, a copper atom, or a platinum atom; and B represents an anionic species) by allowing a bisphosphine derivative represented by general formula (2):

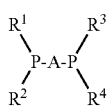
(2)

(wherein R¹ to R⁴ and A have the same meanings as defined above) to react with a metal salt of gold, silver, copper, or platinum.

The present invention provides an anticancer agent containing a transition metal phosphine complex represented by general formula (1):

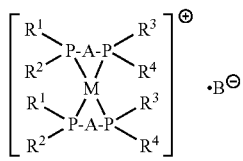
(1)

(wherein R¹s and R³s each represent an alkyl group, a cycloalkyl group, an aryl group, an aralkyl group, a pyridyl group, or a pyrimidyl group; R²s and R⁴s each represent an alkyl group or a cycloalkyl group, provided that each R¹ and each R² are not the same group and that each R³ and each R⁴ are not the same group; As each represent a linear alkylene group or a cis-vinylene group; M represents a gold atom, a silver atom, a copper atom, or a platinum atom; and B represents an anionic species).

BEST MODE FOR CARRYING OUT THE INVENTION

The present invention will be described in detail below on the basis of preferred embodiments.

A transition metal phosphine complex according to the present invention is represented by general formula (1).

R¹s and R³s in general formula (1) each represent an alkyl group, a cycloalkyl group, an aryl group, an aralkyl group, a pyridyl group, or a pyrimidyl group. As the alkyl group, a linear or branched alkyl group having 1 to 20 and preferably 1 to 10 carbon atoms is suitable. Examples thereof include a methyl group, an ethyl group, a propyl group, an isopropyl group, a butyl group, a sec-butyl group, a tert-butyl group, a pentyl group, an isopentyl group, a neopentyl group, and a hexyl group. Examples of the cycloalkyl group include a cyclopentyl group and a cyclohexyl group. Examples of the aryl group include a phenyl group, a tolyl group, a xylyl group, and a naphthyl group. Examples of the aralkyl group include a benzylic group and a phenethyl group. The pyridyl group is a 2-pyridyl group, a 3-pyridyl group, or a 4-pyridyl group. The pyrimidyl group is a 2-pyrimidyl group, a 4-pyrimidyl group, or a 5-pyrimidyl group. Among these, a pyridyl group is preferred. In particular, a 2-pyridyl group is preferred.

R²s and R⁴s in general formula (1) each represent an alkyl group or a cycloalkyl group. As the alkyl group, a linear or branched alkyl group having 1 to 20 and preferably 1 to 10 carbon atoms is suitable. Examples thereof include a methyl group, an ethyl group, a propyl group, an isopropyl group, a butyl group, a sec-butyl group, a tert-butyl group, a pentyl group, an isopentyl group, a neopentyl group, and a hexyl group. Examples of the cycloalkyl group include a cyclopentyl group and a cyclohexyl group. Among these, a linear or branched alkyl group is preferred. In particular, a tert-butyl group is preferred. In general formula (1), each R¹ and each R² are not the same group, and each R³ and each R⁴ are not the same group.

As in general formula (1) each represent a linear alkylene group or a cis-vinylene group. As the linear alkylene group, an alkylene group having 1 to 5 carbon atoms is suitable. Examples thereof include a methylene group, an ethylene group, a trimethylene group, a tetramethylene group, and a pentamethylene group. An ethylene group is preferred.

M in general formula (1) represents a gold, silver, copper, or platinum atom. Among these, a gold atom is particularly preferred.

B in general formula (1) represents an anionic species. Examples thereof include halogen atoms, such as chlorine, bromine, and iodine; tetrafluoroboron; hexafluorophosphate; and perchloric acid. Among these, halogen atoms, such as chlorine, bromine, and iodine, are particularly preferred.

Preferred examples of the transition metal phosphine complex according to the present invention include bis(1,2-bis(tert-butyl(2-pyridyl)phosphino)ethane)gold(I) chloride, bis(1,2-bis(tert-butyl(2-pyrimidyl)phosphino)ethane)gold(I) chloride, bis(1,2-bis(tert-butyl(methyl)phosphino)ethane) gold(I) chloride, bis(1,2-bis(methyl(phenyl)phosphino) ethane)gold(I) chloride, bis(1,2-bis(tert-butyl(2-pyridyl) phosphino)ethane)gold(I) bromide, bis(1,2-bis(tert-butyl(2-pyrimidyl)phosphino)ethane)gold(I) bromide, bis(1,2-bis(tert-butyl(methyl)phosphino)ethane)gold(I) bromide, bis(1,2-bis(methyl(phenyl)phosphino)ethane)gold(I) bromide, bis(1,2-bis(tert-butyl(2-pyridyl)phosphino)ethane)gold(I) iodide, bis(1,2-bis(tert-butyl(2-pyrimidyl)phosphino) ethane)gold(I) iodide, bis(1,2-bis(tert-butyl(methyl)phosphino)ethane)gold(I) iodide, or bis(1,2-bis(methyl(phenyl) phosphino)ethane)gold(I) iodide.

In the present invention, the transition metal phosphine complex of general formula (1) may have an optically active form. An example of the optically active form is a transition metal phosphine complex having phosphorus atoms serving as asymmetric centers, the complex being represented by general formula (4):

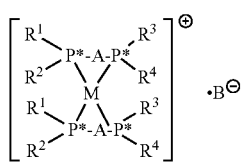
(4)

(wherein $R^1$ to $R^4$, A, B, and M have the same meanings as defined above; and phosphorus atoms functioning as asymmetric center are marked with asterisks). The optically active transition metal phosphine complex of general formula (4) may have an (S,S)-configuration or an (R,R)-configuration. Alternatively, the complex may have a meso-form. Preferred examples of the optically active form include the above-described compounds suitable for the transition metal phosphine complex according to the present invention, the compounds each having an (S,S)-configuration, an (R,R)-configuration, or a meso-form.

A method for producing the transition metal phosphine complex of the present invention will be described below. The transition metal phosphine complex of the present invention may be produced by allowing a bisphosphine derivative represented by general formula (2):

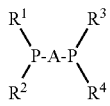
(2)

(wherein $R^1$ to $R^4$ and A have the same meanings as defined above) to react with a transition metal salt of gold, copper, platinum, or silver.

The bisphosphine derivative represented by general formula (2) is a starting material and may be produced by a known method. Examples thereof include the following methods: a method in which according to reaction formula (I):

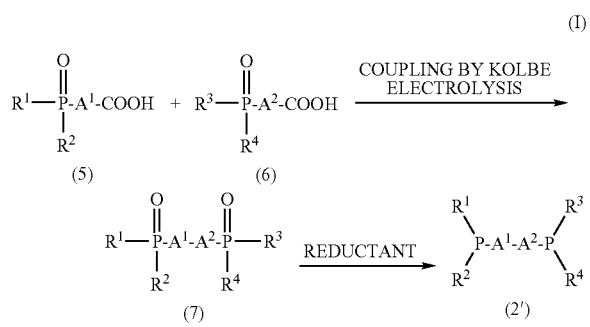
(I)

(wherein $R^1$ to $R^4$ have the same meanings as defined above; and $A^1$ and $A^2$ each represent an alkylene group), after a coupling reaction is performed by Kolbe electrolysis, a reduction reaction is performed with a reductant, such as trichlorosilane or phenylsilane (see Japanese Unexamined Patent Application Publication No. 11-228586 and International Publication No. WO01/046098); a method in which according to reaction formula (II):

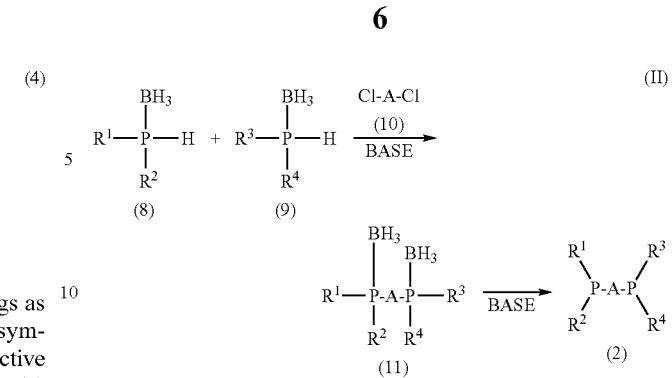
(II)

(wherein $R^1$ to $R^4$ and A have the same meanings as defined above), secondary phosphine borane compounds (compounds (8) and (9)) are allowed to react with a dichlorocompound (compound (10) in the presence of a base, and then the borane moieties are removed with a base, such as ethylamine, diethylamine, or pyrrolidine (see Japanese Unexamined Patent Application Publication No. 2003-300988 and J. Org. Chem., Vol. 65, No. 6, 2000, pages 1877-1880); and a method in which according to reaction formula (III):

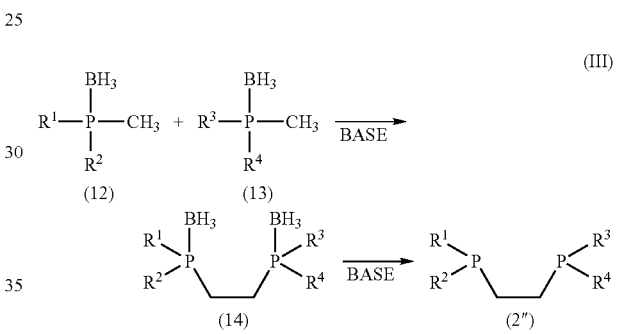
(III)

(wherein $R^1$ to $R^4$ have the same meanings as defined above), after methylphosphine borane compounds (compounds (12) and (13)) are treated with a base, such as n-butyllithium, and then with copper chloride, the borane moieties are removed with a base such as ethylamine, diethylamine, or pyrrolidine (see Japanese Unexamined Patent Application Publication No. 11-80179).

To obtain an optically active form by a reaction according to reaction formula (I), a method in which the racemic-form of a phosphineoxycarboxylic acid (compound (5) or (6)) is treated with an optically active amine such as 1-phenylethylamine to form diastereomeric salts, and the resulting salts are resolved by utilizing the difference in solubility in a solvent to obtain optically active forms may be employed (see WO01/046098 and Japanese Unexamined Patent Application Publication No. 11-228587). To obtain an optically active form by the reaction according to the reaction formula (II) or (III), the reaction according to reaction formula (II) or (III) may be similarly performed with optically active secondary phosphine borane compounds (compounds (8) and (9)) or optically active methylphosphine borane compounds (compounds (12) and (13)) as starting materials. As a method for preparing the optically active secondary phosphine borane compounds (compounds (8) and (9)) or the optically active methylphosphine borane compounds (compounds (12) and (13)), a method in which racemic forms of the secondary phosphine borane compounds (compounds (8) and (9)) or the methylphosphine borane compounds (compounds (12) and (13)) are subjected to optical resolution by common high performance chromatography to obtain optically active compounds corresponding to the secondary phosphine borane compounds (compounds (8) and (9)) or the methylphosphine borane compounds (compounds (12) and (13)) may be employed. Non-limiting examples of a method for preparing the optically active secondary phosphine borane compounds (compounds (8) and (9)) include a method including allowing racemic forms of the secondary phosphine borane compounds (compounds (8) and (9)) to react with a (−)-sparteine-(S)-butyllithium complex, performing oxidation to obtain optically active alcohols of phosphine borane compounds, and performing oxidative decarboxylation to obtain optically active compounds corresponding to the secondary phosphine borane compounds (compounds (8) and (9)) (see J. Org. Chem., Vol. 65, No. 6, 2000, pages 4185-4188); and a method including allowing racemic forms of the secondary phosphine borane compounds (compounds (8) and (9)) to react with an optically active halogenated carbonate in the presence of a base to prepare a diastereomeric mixture of alkoxycarbonylphosphine borane, subjecting alkoxycarbonylphosphine borane to optical resolution by recrystallization, and treating the resulting compounds with an alkaline agent to obtain optically active forms corresponding to the secondary phosphine borane compounds (compounds (8) and (9)) (see Japanese Unexamined Patent Application Publication No. 2003-300988).

Examples of the transition metal salt usable as the other starting material include halides, nitrates, perchlorates, tetrafluoroborates, and hexafluorophosphates of gold, silver, copper, and platinum. Preferred examples of the metal salt of gold include chloroauric acid, gold(I) chloride, and tetrabutylammonium chloride·gold(I) chloride (see "Jikken Kagaku Koza 21 (Courses in Experimental Chemistry), 5th Ed.", edited by The Chemical Society of Japan, published by Maruzen Co., Ltd., published on March 30, Heisei 16 (2004), p.p. 366-380; and Aust. J. Chemm., 1997, 50, p.p. 775-778). Preferred examples of the metal salt of copper include copper (I) chloride, copper(I) bromide, and copper(I) iodide (see "Jikken Kagaku Koza 21 (Courses in Experimental Chemistry), 5th Ed.", edited by The Chemical Society of Japan, published by Maruzen Co., Ltd., published on March 30, Heisei 16 (2004), p.p. 349-361). Preferred examples of the transition metal salt of platinum include platinum(II) chloride, sodium tetrachloroplatinate(II), and potassium tetrachloroplatinate(II) (see "Jikken Kagaku Koza 21 (Courses in Experimental Chemistry), 5th Ed.", edited by The Chemical Society of Japan, published by Maruzen Co., Ltd., published on March 30, Heisei 16 (2004), p.p. 327-348). Preferred examples of the transition metal salt of silver include silver(I) chloride, silver(I) bromide, and silver(I) iodide (see "Jikken Kagaku Koza 21 (Courses in Experimental Chemistry), 5th Ed.", edited by The Chemical Society of Japan, published by Maruzen Co., Ltd., published on March 30, Heisei 16 (2004), p.p. 361-366). The transition metal salts may be anhydrides or hydrates.

In general, the reaction between the bisphosphine derivative represented by general formula (2) and the transition metal salt may be performed by allowing the transition metal salt to react with 1 to 5 moles and preferably 1.8 to 2.2 moles of the bisphosphine derivative per mole of the transition metal salt at a reaction temperature of −20° C. to 60° C. and preferably 0° C. to 25° C. for a reaction time of 0.5 to 48 hours and preferably 1 to 3 hours in a solvent such as acetone, acetonitrile, methanol, or ethanol. After completion of the reaction, if necessary, common purification is performed to obtain a product.

In the transition metal phosphine complex of the present invention, a complex in which B in general formula (1) represents a halogen atom is prepared, and then the complex is allowed to react with a desired inorganic acid, organic acid, or an alkali metal salt thereof to covert B into another anion (see Japanese Unexamined Patent Application Publication Nos. 10-147590, 10-114782, and 61-10594).

The transition metal phosphine complex of the present invention has excellent anticancer activity as described below and thus can be used as an anticancer agent.

An anticancer agent of the present invention contains one or more transition metal phosphine complexes represented by general formula (1) or optically active forms thereof.

The type of cancer for which the anticancer agent of the present invention can be used is not particularly limited. Examples thereof include malignant melanoma, malignant lymphoma, gastrointestinal cancer, lung cancer, esophageal cancer, gastric cancer, colon cancer, rectal cancer, colonic cancer, ureter tumors, gallbladder cancer, cholangiocarcinoma, biliary tract cancer, breast cancer, hepatoma, pancreas cancer, orchioncus, cancer of the upper jaw, tongue cancer, lip cancer, oral cancer, pharyngeal cancer, laryngeal cancer, ovarian cancer, uterine cancer, prostate cancer, thyroid cancer, brain tumors, Kaposi's sarcoma, angioma, leukemia, polycythemia vera, neuroblastoma, retinoblastoma, myeloma, bladder tumor, sarcoma, osteosarcoma, myosarcoma, skin cancer, basal cell carcinoma, skin appendage carcinoma, metastatic skin cancer, and cutaneous melanoma. The anticancer agent may be used for benign tumors as well as malignant tumors. The anticancer agent of the present invention may be used to inhibit cancer metastasis. In particular, the anticancer agent is useful as a cancer metastasis suppressor used after surgery.

The anticancer agent of the present invention may be administered to humans or animals in various routes. Examples of the routes include oral administration; and parenteral administration, such as injections, e.g., an intravenous injection, an intramuscular injection, a hypodermic injection, and an intradermal injection, intrarectal administration, and transmucosal administration. Examples of formulations suitable for oral administration include tablets, pills, granules, powders, capsules, liquid formulations, suspensions, emulsions, and syrups. Examples of pharmaceutical compositions suitable for parenteral administration include injections, drops, nasal drops, sprays, inhalants, and suppository; and transdermal absorptive formulations such as ointments, creams, powdery liniments, liquid liniments, and patches. Furthermore, the formulation may be a depot preparation such as an implantable pellet or a depot preparation by the known art. Among these, a preferred administration route and formulation are appropriately selected by a doctor in response to, for example, the age, sex, constitution, symptoms, and timing of treatment of a patient.

To prepare the inventive anticancer agent that is in the form of a solid formulation, such as tablets, pills, powders, or granules, the transition metal phosphine complex may be appropriately mixed with a proper additive according to a usual manner. Examples of the additive include excipients, such as lactose, sucrose, D-mannitol, corn starch, synthetic or natural gum, and crystalline cellulose; binders, such as starch, hydroxypropylcellulose, hydroxypropylmethylcellulose, gum arabic, gelatin, and polyvinylpyrrolidone; disintegrators, such as carboxymethylcellulose calcium, carboxymethylcellulose sodium, starch, corn starch, and sodium alginate; lubricants, such as talc, magnesium stearate, and sodium stearate; bulking agents, such as calcium carbonate, sodium carbonate, calcium phosphate, and sodium phosphate; and diluents. For example, according to need, tablets may be subjected to sugar coating, gelatin coating, enteric coating, or film coating with a coating agent, such as hydroxypropylmethylcellulose, saccharose, polyethylene glycol, or titanium oxide.

To prepare the inventive anticancer agent that is in the form of a liquid formulation, such as an injection, an eye drop, a nasal drop, an inhalant, a spray, a lotion, a syrup, a solution, a suspension, or an emulsion, the transition metal phosphine complex is dissolved in an appropriate buffer solution, such as purified water or a phosphate buffer solution; a physiological salt solution, such as physiological saline, a Ringer's solution, or a Locke's solution; a vegetable oil, such as cacao butter, sesame oil, or olive oil; or an organic solvent, such as mineral oil, a higher alcohol, a higher fatty acid, or ethanol. According to need, the resulting mixture may further contain an emulsifier such as cholesterol, a suspending agent such as gum arabic, a dispersing agent, a wetting agent, a surfactant such as polyoxyethylene hydrogenated castor oil or polyethylene glycol, a solubilizer such as sodium phosphate, a stabilizer such as sugar, a sugar alcohol, or albumin, a preservative such as paraben, an isotonizing agent such as sodium chloride, glucose, or glycerol, a buffer, a soothing agent, an adhesion prevention agent, a moisturizing agent, an antioxidant, a colorant, a sweetener, a flavor, or an aromatic substance. Thereby, the anticancer agent can be prepared in the form of a sterile aqueous solution, nonaqueous solution, suspension, ribosome, or an emulsion. Preferably, the injections each have a physiological pH and preferably in the range of 6 to 8.

To prepare the inventive anticancer agent that is in the form of a semi-solid preparation, such as a lotion, a cream, or an ointment, the transition metal phosphine complex may be appropriately mixed with fat, fatty oil, lanolin, Vaseline, paraffin, wax, plaster, a resin, plastic, glycol, a higher alcohol, glycerol, water, an emulsifier, a suspending agent, or the like.

The content of the transition metal phosphine complex in the anticancer agent of the present invention varies depending on a dosage form, severity, a target dose, and the like. In general, the content is 0.001 to 80 percent by weight and preferably 0.1 to 50 percent by weight relative to the total weight of the formulation.

The dosage of the anticancer agent of the present invention is appropriately determined by a doctor in response to, for example, the age, sex, body weight, and symptoms of a patient, and the administration route. In general, the active ingredient is administered in a dose of about 1 µg/kg to 1,000 mg/kg and preferably about 10 µg/kg to 10 mg/kg per adult per day. The above-described dose of the agent may be administered in single or divided doses (e.g., about 2 to 4 times) per day.

The anticancer agent of the present invention may be used in combination with known chemotherapy, surgical treatment, radiation therapy, thermotherapy, immunotherapy, or the like.

Example 1

The present invention will be described in detail below by means of examples but is not limited thereto.

Reference Example 1

Synthesis of (R,R)-1,2-bis(boranato(tert-butyl)-(2-pyridyl)phosphino)ethane and rac-(or meso-)1,2-bis(boranato(tert-butyl)-(2-pyridyl)phosphino)ethane Synthesis of (R,R)-1,2-bis(boranato-tert-butyl(2-pyridyl)phosphino)ethane (R,R)-1,2-Bis(boranato-tert-butylphosphino)ethane (0.94 g, 4 mmol) prepared according to a known method (Tet. Lett., 2002, 43, 7735) and dehydrated THF (24 mL) were fed to a 50-mL two-neck flask from which water had been sufficiently removed and which had been filled with a nitrogen gas. The mixture was cooled to 0° C. in an ice bath. A paraffin solution of 60% sodium hydride (0.48 g, 12 mmol) was added thereto in a single procedure. After stirring was continued for 10 minutes, 2-chloropyridine (1.82 g, 16 mmol) was added thereto. After stirring was continued for 30 minutes, the ice bath was removed. Then the reaction was performed at room temperature for 21 hours. Water (12 mL) was added thereto to terminate the reaction. After an organic layer was collected, an aqueous layer was subjected to extraction with ethyl acetate (10 mL). The resulting organic layers were dehydrated and then subjected to separation by silica-gel column chromatography (hexane:ethyl acetate=9:1) to obtain (R,R)-1,2-bis(boranato-tert-butyl(2-pyridyl)phosphino)ethane (0.70 g, yield: 44%, 89% e.e.) as a white solid.

(Identification Data)
$^1$H-NMR (300.4 MHz, CDCl$_3$): δ=1.09 (s, 18H), 2.07-2.16 (m, 2H), 2.36-2.43 (m, 2H), 7.32-7.37 (m, 2H), 7.73-7.79 (m, 2H), 7.98-8.00 (m, 2H), 8.54-8.55 (m, 2H)
$^{31}$P NMR (121.5 MHz, CDCl$_3$): δ=37.9
IR (KBr, cm$^{-1}$): 3045, 2965, 2931, 2901, 2869, 2368, 1573, 1456, 1425, 1065, 766
Mass (FAB, POS): m/z 389. (M$^+$+H)
(Analysis Condition for Enantiomeric Excess with Chiral HPLC)
Column: Daicel AD-H, UV wavelength: 254 nm, Flow: 1.0 mL/min, 35° C.
Mobile phase: Hex:2-propanol=99:1
(R,R)-form: 14.8 min, (S,S)-form: 26.0 min Synthesis of rac-1,2-bis(boranato-tert-butyl(2-pyridyl)phosphino)ethane and meso-1,2-bis(boranato-tert-butyl(2-pyridyl)phosphino)ethane Tetramethylethylenediamine (0.71 g, 6.1 mmol) and dehydrated diethyl ether (13 mL) were fed to a 50-mL two-neck flask from which water had been sufficiently removed and which had been filled with a nitrogen gas. The mixture was cooled to −78° C. s-BuLi (6.3 mL, 6.1 mmol) was added dropwise thereto over a period of 10 minutes. The resulting mixture was stirred for 1 hour. A dehydrated ether solution (5 mL) of tert-butylmethyl(2-pyridyl)phosphine borane (1.0 g, 5.1 mmol) was added thereto. The resulting mixture was stirred for 3 hours. Cupric chloride (1.03 g, 7.7 mmol) that had been dried under reduced pressure was added thereto. The resulting mixture was stirred for 30 minutes. The mixture was warmed to 0° C. and stirred for 2 hours. Then 29% aqueous ammonia (7 mL) was added thereto to terminate the reaction. After an organic layer was collected, an aqueous layer was extracted twice with ethyl acetate (10 mL). These organic layers were washed with 5% aqueous ammonia (7 mL) and 2 N hydrochloric acid (7 mL) and then dehydrated. The resulting organic layers were subjected to separation by silica-gel column chromatography (hexane:ethyl acetate=9:

1) to obtain rac-1,2-bis(boranato-tert-butyl(2-pyridyl)phosphino)ethane (0.15 g, yield: 15%) and meso-1,2-bis(boranato-tert-butyl(2-pyridyl)phosphino)ethane (0.19 g, yield: 19%), which were each a white solid.

(Identification Data): meso-1,2-Bis(boranato-tert-butyl(2-pyridyl)phosphino)ethane $^1$H-NMR (300.4 MHz, CDCl$_3$): δ=1.06 (s, 18H), 1.71-1.74 (m, 2H), 2.77-2.80 (m, 2H), 7.32-7.36 (m, 2H), 7.71-7.77 (m, 2H), 7.93-7.95 (m, 2H), 8.73-8.74 (m, 2H), $^{31}$P NMR (121.5 MHz, CDCl$_3$): δ=38.4

IR (KBr, cm$^{-1}$): 3054, 2971, 2930, 2903, 2869, 2382, 2351, 1571, 1425, 1067, 756

Mass (FAB, POS): m/z 389. (M$^+$+H)

Example 1

Synthesis of bis(rac-1,2-bis(tert-butyl(2-pyridyl)phosphino)ethane)gold(I) chloride Rac-1,2-bis(boranato-tert-butyl(2-pyridyl)phosphino)ethane (1.11 g, 2.9 mmol) prepared in Reference Example 1 and degassed pyrrolidine (8.2 g, 115 mmol) were fed to a 25-mL two-neck flask which had been filled with a nitrogen gas. The mixture was stirred at 40° C. for 8 hours. Pyrrolidine was distilled off. The mixture was subjected to separation by alumina-gel column chromatography (hexane:acetone=15:1) under a stream of nitrogen to obtain rac-1,2-bis(tert-butyl(2-pyridyl)phosphino)ethane (0.94 g, yield: 92%) as a white solid.

A 20-mL dropping funnel was attached to a 25-mL two-neck flask which had been filled with a nitrogen gas. Sodium chloroaurate dihydrate (0.20 g, 0.5 mmol), degassed acetone (0.8 mL), and degassed water (2.0 mL) were fed to the flask. Then β-thiodiglycol (0.12 g, 1 mmol) was added thereto. The mixture was stirred for 15 minutes and then cooled to −5° C. An acetone solution (12 mL) of rac-1,2-bis(tert-butyl(2-pyridyl)phosphino)ethane (0.36 g, 1.0 mmol) was added dropwise over a period of 30 minutes from the dropping funnel. The resulting solution was evaporated to dryness. Methanol (5 mL) and diethyl ether (15 mL) were added thereto. The resulting mixture was allowed to stand overnight at 0° C. The resulting white solid was filtered and dried under reduced pressure to obtain bis(rac-1,2-bis(tert-butyl(2-pyridyl)phosphino)ethane)gold chloride (hereinafter, referred to as "Compound (1)) (0.37 g, yield: 81%).

(Identification Data) [rac-1,2-Bis(tert-butyl(2-pyridyl)phosphion)ethane]

$^1$H-NMR (300.4 MHz, CDCl$_3$): δ=0.92 (s, 18H), 1.61-1.80 (m, 2H), 2.32-2.44 (m, 2H), 7.25-8.78 (m, 8H)

$^{31}$PNMR (121.5 MHz, CDCl$_3$): δ=12.9

Mass (GC-EI, POS): m/z 303. (M$^+$-tBu)

(Identification Data) [Bis(rac-1,2-bis(tert-butyl(2-pyridyl)phosphino)ethane)gold(I) chloride]

$^1$H-NMR (300.4 MHz, CDCl$_3$): δ=1.20 (s, 36H), 2.6-3.2 (m, 8H), 7.6 (m, 4H), 8.3 (m, 4H), 8.5 (m, 4H), 8.8 (m, 4H)

$^{31}$PNMR (121.5 MHz, CDCl$_3$): δ=67.3

Mass (FAB, POS): m/z 917. (M$^+$-Cl$^-$)

Example 2

Synthesis of bis(meso-1,2-bis(tert-butyl(2-pyridyl)phosphino)ethane)gold(I) chloride A reaction was performed as in Example 1, except that meso-1,2-bis(boranato-tert-butyl(2-pyridyl)phosphino)ethane prepared in Reference Example 1 was used, thereby forming bis(meso-1,2-bis(tert-butyl(2-pyridyl)phosphino)ethane)gold(I) chloride (hereinafter, referred to as "Compound (2)) (0.53 g, yield: 90%).

(Identification Data)

$^1$H-NMR (300.4 MHz, CDCl$_3$): δ=1.20 (s, 36H), 3.10-3.20 (m, 4H), 3.40-3.50 (m, 4H), 7.30-7.34 (m, 4H), 7.76-7.81 (m, 4H), 8.14-8.17 (m, 4H), 8.31-8.34 (m, 4H)

$^{31}$P NMR (121.5 MHz, CDCl$_3$): δ=55.3

Mass (FAB, POS): m/z 917. (M$^+$-Cl$^-$)

Example 3

Synthesis of bis((R,R)-1,2-bis(tert-butyl(2-pyridyl)phosphino)ethane)gold(I) chloride A reaction was performed as in Example 1, except that rac-1,2-bis(boranato-tert-butyl(2-pyridyl)phosphino)ethane prepared in Reference Example 1 was used, thereby forming bis(meso-1,2-bis(tert-butyl(2-pyridyl)phosphino)ethane)gold(I) chloride (hereinafter, referred to as "Compound (3)) (0.53 g, yield: 90%).

(Identification Data)

$^1$H-NMR (300.4 MHz, CDCl$_3$): δ=1.20 (s, 36H), 3.10-3.20 (m, 4H), 3.40-3.50 (m, 4H), 7.30-7.34 (m, 4H), 7.76-7.81 (m, 4H) 8.14-8.17 (m, 4H), 8.31-8.34 (m, 4H)

$^{31}$PNMR (121.5 MHz, CDCl$_3$): δ=55.3

Mass (FAB, POS): m/z 917. (M$^+$-Cl$^-$)

Reference Example 2

Synthesis of (R,R)-1,2-bis(boranato-tert-butyl(2-pyrimidyl)phosphino)ethane (R,R)-1,2-Bis(boranato-tert-butylphosphino)ethane (0.94 g, 4 mmol) and dehydrated THF (12 mL) were fed to a 50-mL two-neck flask from which water had been sufficiently removed and which had been filled with a nitrogen gas. The mixture was cooled to 0° C. in an ice bath. A paraffin solution of 60% sodium hydride (0.48 g, 12 mmol) was added thereto in a single procedure. After stirring was continued for 10 minutes, 2-chloropyrimidine (1.83 g, 16 mmol) was added thereto. After stirring was continued for 30 minutes, the ice bath was removed. The mixture was warmed to 40° C. The reaction was performed for 6 hours. Water (5 mL) was added thereto to terminate the reaction. After an organic layer was collected, an aqueous layer was subjected to extraction twice with ethyl acetate (10 mL). The resulting organic layers were dehydrated and then subjected to separation by silica-gel column chromatography (hexane:ethyl acetate=4:1) to obtain (R,R)-1,2-bis(boranato-tert-butyl(2-pyrimidyl)phosphino)ethane (0.62 g, yield: 40%) as a white solid.

(Identification Data)

$^1$H-NMR (300.4 MHz, CDCl$_3$): δ=1.20 (s, 18H), 2.25-2.35 (m, 2H), 2.66-2.73 (m, 2H), 7.35-7.39 (m, 2H), 8.82-8.85 (m, 4H)

$^{31}$P NMR (121.5 MHz, CDCl$_3$): δ=45.5

IR (KBr): 2963, 2901, 2868, 2370, 2339, 1553, 1460, 1386, 1060, 767

Mass (FAB, POS): m/z 391. (M$^+$+H)

Example 4

Synthesis of bis((R,R)-1,2-bis(tert-butyl(2-pyrimidyl)phosphino)ethane)gold(I) chloride (R,R)-1,2-Bis(boranato-tert-butyl(2-pyrimidyl)phosphino)ethane (0.20 g, 0.5 mmol) prepared in Reference Example 2, degassed 1-methylpyrrolidine (1.7 g, 20 mmol), and degassed chloroform (5 mL) were fed to a 25-mL two-neck flask which had been filled with a nitrogen gas. The mixture was stirred at 70° C. for 4 hours, Then 1-methylpyrrolidine and chloroform were distilled off. The mixture was subjected to separation by alumina-gel column chromatography (dichloromethane) under a stream of nitrogen to obtain (R,R)-1,2-bis(tert-butyl(2-pyrimidyl)phosphino)ethane (0.15 g, yield: 84%) as a white solid.

Degassed chloroform (4 mL) and (R,R)-1,2-bis(tert-butyl (2-pyrimidyl)phosphino)ethane (0.15 g) were fed to a 25-mL two-neck flask which had been filled with a nitrogen gas to obtain a clear, colorless solution. Tetrabutylammonium dichloroaurate(I) (0.10 g, 0.2 mmol) was added thereto. The resulting mixture was stirred for 17 hours at room temperature. After the solvent was distilled off, recrystallization was performed with ethanol-diethyl ether to obtain bis(rac-1,2-bis(tert-butyl(2-pyrimidyl)phosphino)ethane)gold(I) chloride (hereinafter, referred to as "Compound (4)) (0.04 g, yield: 21%).

(Identification Data)
$^1$H-NMR (300.4 MHz, CDCl$_3$): δ=1.17 (s, 36H), 2.07-2.20 (m, 4H), 2.92-2.95 (m, 4H), 7.40-7.42 (m, 4H), 8.82-8.92 (m, 8H)
$^{31}$PNMR (121.5 MHz, CDCl$_3$): δ=49.9
Mass (FAB, POS): m/z 922. (M$^+$-Cl$^-$)

Reference Example 3

Synthesis of
1,2-bis(phenyl(2-pyridyl)phosphino)ethane

Synthesis of methylphenyl(2-pyridyl)phosphine borane

Phenylphosphine (10 g, 90 mmol) and dehydrated THF (400 mL) were fed to a 1-L four-neck flask under a stream of nitrogen. The mixture was cooled to −20° C. and stirred. Then n-BuLi (58 mL, 1.60 M, 93 mmol) was added thereto from a dropping funnel. The resulting mixture was stirred for 1 hour. Methyl iodide (13.28 g, 93 mmol) was added thereto with a syringe over a period of 3 minutes. The reaction mixture was warmed to room temperature. The reaction was performed for 1 hour. The reaction flask was cooled to −20° C. again. Then n-BuLi (60 mL, 1.60 M, 95 mmol) was added thereto from the dropping funnel. The resulting mixture was stirred for 1 hour. Next, 2-chloropyridine (10.83 g, 95 mmol) was added thereto with a syringe over a period of 3 minutes. After stirring was continued for 10 minutes at the temperature, the reaction flask was warmed to 50° C. Stirring was performed for another 1 hour to perform the reaction. The reaction flask was cooled to 0° C. again. A THF solution (132 mL, 1.02 M, 135 mmol) of a borane·THF complex was added thereto with a syringe. The reaction was performed for 1 hour. The reaction mixture was carefully poured onto crashed ice (200 g) to terminate the reaction. After the solution was stirred until foaming was stopped, an organic layer was separated with a separating funnel. An aqueous layer was extracted three times with ethyl acetate (50 mL). The combined organic layers were washed twice with deionized water (200 mL) and then saturated brine (400 mL) and dried over anhydrous sodium sulfate. The solvent was distilled off to obtain a crude product (20.3 g). This was subjected to separation by silica-gel column chromatography (hexane:ethyl acetate=9:1 to 4:1) to separate a target compound. Evaporation of the solvent provided the oily title compound (16.7 g, yield: 86%).

Synthesis of
1,2-bis(boranatophenyl(2-pyridyl)phosphino)ethane

Methylphenyl(2-pyridyl)phosphine borane (16.3 g, 76 mmol) prepared above and dehydrated THF were fed to a 750-mL four-neck flask under a stream of nitrogen. The mixture was cooled to −78° C. s-BuLi (84 mL, 1.0 M, 84 mmol) was added dropwise to the flask with a dropping funnel over a period of 20 minutes. The reaction mixture was stirred for 2 hours while the temperature of the mixture was maintained at −78° C. Well-dried copper (II) chloride (15.33 g, 114 mmol) was added thereto in a single procedure. After the mixture was stirred for another 30 minutes at the temperature, the reaction flask was warmed to 0° C. over a period of 2 hours. Concentrated aqueous ammonia (150 mL) was added to the reaction flask to terminate the reaction. An organic layer was separated with a separating funnel. An aqueous layer was extracted three times with ethyl acetate (100 mL). The organic layer extracted was washed twice with 5% aqueous ammonia (150 mL), deionized water (100 mL), and saturated brine (100 mL) and then dehydrated over anhydrous sodium sulfate. Evaporation of the solvent provided a crude product. The crude product was roughly purified by silica-gel column chromatography (chloroform) and then recrystallized from a mixed solvent of chloroform/hexane to obtain the title compound (11.3 g, yield: 69%) as white crystals, the compound having a ratio of the racemic-form to the meso-form of about 1:1.
(Identification Data)
Melting point: 130° C. (decomposed)
$^1$H NMR (CDCl$_3$): δ=1.23 (d, J$_{HB}$=12.2 Hz, 18H), 1.83 (m, 2H) 1.07 (m, 2H), 2.21 (m, 4H), 2.43 (m, 2H), 2.77 (m, 2H), 4.26 (s, 2H), 5.74 (d, J=25.1 Hz, 2H), 5.75 (d, J=4.6 Hz, 2H)
$^{31}$P NMR ($^1$H decoupled, CDCl$_3$): δ=114.8 (d, J$_{P-Rh}$=148 Hz), 143.7 (h, J$_{P-F}$=711 Hz)
IR (KBr): 2940, 1465, 1310, 1180, 840, 560 cm$^{-1}$.

Synthesis of
1,2-bis(phenyl(2-pyridyl)phosphino)ethane

Under a stream of nitrogen, 1,2-bis(boranatophenyl(2-pyridyl)phosphino)ethane (4.28 g, 10 mmol) and pyrrolidine (13 mL) were fed to a 50-mL two-neck flask. The mixture was heated to 70° C. in an oil bath and stirred for 3 hours. After completion of the reaction, evaporation of excess pyrrolidine with an evaporator provided a residue. The resulting residue was roughly purified by basic-alumina column chromatography (hexane:ethyl acetate=5:1) to obtain a crude product. The crude product was recrystallized from sufficiently degassed ethanol to obtain the title compound (3.0 g, yield: 74%) as white crystals, the compound having a ratio of the racemic-form and the meso-form of about 1:1.
(Identification Data)
$^{31}$P NMR ($^1$H decoupled, CDCl$_3$): δ=−9.2(s), −9.0(s)

Comparative Example 1

Synthesis of bis[1,2-bis(phenyl(2-pyridyl)phosphino) ethane]gold(I) chloride

In a 100-mL two-neck flask, 1,2-bis(phenyl(2-pyridyl) phosphino)ethane (2.40 g, 6 mmol) prepared in Reference Example 3 was dissolved in sufficiently degassed chloroform (25 mL) under a stream of nitrogen. A chloroform solution (25 mL) of a gold(I) chloride-tetrabutylammonium chloride adduct (1.53 g, 6 mmol) was added thereto at room temperature over a period of 1 hour with a dropping funnel while the reaction solution was stirred. The reaction mixture was stirred for another 2 hours and then transferred into a separating funnel. The reaction mixture was washed three times with degassed deionized water (20 mL) and saturated brine (20 mL) and then dehydrated with anhydrous sodium sulfate. Evaporation of chloroform with an evaporator provided the title compound trihydrate (hereinafter, referred to as "Compound (5)") (3.13 g) as a yellow-green solid. The yield was 96%.

(Identification Data)

$^1$H NMR (CDCl$_3$): δ=2.2-3.4 (m, 8H), 6.4-7.6 (m, 32H), 8.4-8.6 (m, 4H)

$^{31}$PNMR ($^1$H decoupled, CDCl$_3$): δ=21.8-23.4(m); MS (FAB) (M–Cl)$^+$ 997.

TABLE 1

|  | R1 and R3 | R2 and R4 | A | M | B |
|---|---|---|---|---|---|
| Compound(1) | Racemic-form | 2-Pyridyl group | tert-Butyl group | Ethylene group | Au | Cl |
| Compound(2) | Meso-form | 2-Pyridyl group | tert-Butyl group | Ethylene group | Au | Cl |
| Compound(3) | R,R-form | 2-Pyridyl group | tert-Butyl group | Ethylene group | Au | Cl |
| Compound(4) | R,R-form | 2-Pyrimidyl group | tert-Butyl group | Ethylene group | Au | Cl |
| Compound(5) | Racemic-form | 2-Pyridyl group | Phenyl | Ethylene group | Au | Cl |

Example 5

Evaluation of Water Solubility

Compounds (1) to (4) obtained in Examples 1 to 4, Compound (5) obtained in Comparative Example 1, and cisplatin were evaluated for water solubility.

Deionized water was added to each of Compounds (1) to (5) and cisplatin in such a manner that each concentration was 1×10$^{-2}$ M/L. Each of the resulting mixtures was diluted ten times. Water solubility was visually evaluated according to the following three criteria: Highly soluble (Excellent); Less soluble (Fair); Insoluble (Poor). Table 2 shows the results.

TABLE 2

|  | Compound (1) | Compound (2) | Compound (3) | Compound (4) | Compound (5) | Cisplatin |
|---|---|---|---|---|---|---|
| Water solubility | Excellent | Excellent | Excellent | Excellent | Fair | Fair |

Table 2 clearly shows that the transition metal phosphine complexes of the present invention have extremely high water solubility compared with that of cisplatin.

Example 6

Evaluation of Anticancer Property 1

Compounds (1) to (3) obtained in Examples 1 to 3, Compound (5) obtained in Comparative Example 1, and cisplatin were evaluated for anticancer properties according to the following method.

Human acute myelocytic leukemia cells cancer cells HL-60 was used as cancer cells. The cells were cultured in Rosewell Park Memorial Institute medium (RPMI 1640) supplemented with 10% fetal bovine serum, 1% antibiotic, and an antifungal agent in an atmosphere of 5% carbon dioxide in a moist incubator at 37° C.

Cells were washed with PBS. After the number of cells was determined, a suspension (1×10$^6$ cells/mL) was prepared with the same medium. The suspension was seeded in a sterile 96-well microplate at a density of 50,000 cells/well.

A transition metal phosphine complex solution prepared by completely dissolving each transition metal phosphine complex obtained in each of Examples 1 to 3 and Comparative Example 1 in water or dimethyl sulfoxide or a cisplatin solution (Comparative Example 2) was added. The wells were further cultured in the incubator for 24 hours.

The number of viable cells was determined by a modified Mosmann method (T. Mosmann, J. Immunnol. Method (1983)65, 55-63). That is, a solution of a tetrazolium salt (3,[4,5-dimethylthiazole-2-yl]-2,5-diphenyltetrazolium bromide, MTT) was added thereto. The wells were cultured for another 3 hours under the same conditions. Formazan crystals formed by the enzyme activity of mitochondria in the cells were dissolved in 0.04 mol/HCl/isopropyl alcohol. The absorbance of each well was measured at 595 nm with a microplate reader (Bio-Rad 550). To remove the background, the absorbance of each well was measured at 630 nm. The absorbance at 630 nm was subtracted from the actual measured value. This is determined to be the number of viable cells. Then 50% inhibitory concentration (IC$_{50}$) was calculated. Table 2 shows the results. For the values shown in Table 3, each of Compounds 1 to 3 was assayed three times, and the average value was shown. Cisplatin was assayed twice, and the average value was shown.

TABLE 3

|  | IC$_{50}$(μM/L) |
|---|---|
| Compound (1) | 4.51 |
| Compound (2) | 5.13 |
| Compound (3) | 3.58 |
| Compound (5) | 3.56 |
| Cisplatin | 12.6 |

Table 3 clearly shows that the transition metal phosphine complexes of the present invention have excellent anticancer properties compared with that of cisplatin.

Example 7

Evaluation of Anticancer Property 2

Compounds (2) and (3) obtained in Examples 2 and 3 were assayed as in Evaluation 1 with HCS-4 (cells derived from human tongue cancer, medium: RPMI 1640+10% FBS), COLO205 (cells derived from human colon, medium: RPMI-1640+10% FBS), and SH-10-TC (cells derived from human gastric cancer, medium: RPMI-1640+10% FBS). Then 50% inhibitory concentration ($IC_{50}$) was calculated. Table 4 shows the results.

TABLE 4

| | $IC_{50}$(μM/L) | | |
|---|---|---|---|
| | Cell derived from human tongue cancer | Cell derived from human colon | Cell derived from human gastrict cancer |
| Compound (2) | 1.4 | 2.2 | 1.2 |
| Compound (3) | 3.5 | 1.5 | 0.9 |

Table 4 clearly shows that the transition metal phosphine complexes of the present invention also have anticancer activity against the cells derived from human tongue cancer, cells derived from human colon, and cells derived from human gastric cancer.

Example 8

Toxicity Test

Comparative test for toxicity of Compounds (1), (2), (3), and (5) and cisplatin was performed by single oral administration to rats.

After female Sprauge-Dawley SPF rats (CrJ:CD (SD)) were quarantined and acclimated for about a week, healthy 8-week-old rats were selected in groups of five rats. Each of the rats fasted overnight before administration received a single oral dose of 20, 50, 100, or 300 mg/kg of one of Compounds (1) to (4) or 10, 20, 50, or 100 mg/kg of cisplatin with corn oil as a solvent. The rats were observed at 10 and 30 minutes and 1, 2, and 4 hours after administration, then observed daily for 14 days. Lethal dose 50% ($LD_{50}$) was determined from the survival rate of the rats. Table 5 shows the results.

TABLE 5

| | LD50 |
|---|---|
| Compound(1) | 300 mg/kg or more |
| Compound(2) | 300 mg/kg or more |
| Compound(3) | 300 mg/kg or more |
| Compound(5) | 100 to 300 mg/kg |
| Cisplatin | 20 to 50 mg/kg |

From the results shown in Table 5, none of the rats that were received the inventive transition metal phosphine complexes (Compounds (1) to (3)) died at the end of 14 days. During this period, no specific change in general conditions, a body weight shift, and the finding of viscera was observed. Thereby, it was suggested that the phosphine-gold complexes of the present invention have low toxicity.

On the other hand, in Compound (5), no death was observed in the 20 and 50 mg/kg groups. However, in the 100 mg/kg group, one rat died at 5 days after administration. The remaining four rats survived up to the end of the test period. In the 300 mg/kg group, three rats died by day 2. The remaining two rats survived up to the end of the test period. Therefore, it was suggested that Compound (5) have toxicity higher than those of the inventive phosphine-gold complexes (Compounds (1) to (3)).

Example 9

Production of Powder

A sample (50 g) of each of Compounds (1) to (4) prepared as in Examples 1 to 4, lactose (400 g), and corn starch (50 g) were mixed with a blender to form a powder.

Example 10

Production of Granule

A sample (50 g) of each of Compounds (1) to (4) prepared as in Examples 1 to 4, lactose (250 g), and low substituted hydroxypropylcellulose (50 g) were mixed. After an aqueous solution of 10% hydroxypropylcellulose (150 g) was added thereto, the resulting mixture was kneaded. The mixture was granulated and dried with an extruding granulator to form granules.

Example 11

Production of Tablet

A sample (50 g) of each of Compounds (1) to (4) prepared as in Examples 1 to 4, lactose (250 g), corn starch (120 g), crystalline cellulose (75 g), and magnesium stearate (5 g) were mixed with a blender. The mixture was compressed on a tablet machine to form tablets.

Example 12

Production of Capsule

A sample (25 g) of each of Compounds (1) to (4) prepared as in Examples 1 to 4, lactose (300 g), corn starch (170 g), and magnesium stearate (5 g) were mixed with a V-blender. Then 180 mg of the mixture was filled into each capsule of size 3 to form capsules.

Example 13

Production of Injection

A sample (100 mg) of each of Compounds (1) to (4) prepared as in Examples 1 to 4 and glucose (100 mg) were dissolved in purified water (2 mL). The solution was filtered. The resulting filtrate was dispensed into 2-ml ampoules. After the ampoules were sealed off, sterilization was performed to obtain injections.

Example 14

Production of Lotion

A sample (1 g) of each of Compounds (1) to (4) prepared as in Examples 1 to 4, ethanol (3 g), hydroxyethylcellulose (0.2 g), and methyl parahydroxybenzoate (0.1 g) were mixed in purified water (100 mL) to form a lotion.

Example 15

Production of Ointment

A sample (2 g) of each of Compounds (1) to (4) prepared as in Examples 1 to 4, liquid paraffin (6 g), beeswax (2 g), self-emulsifying glyceryl monostearate (3 g), and white petrolatum (5 g) were heated to melt and disperse, thereby forming an ointment.

Example 16

Production of Cream

A sample (2 g) of each of Compounds (1) to (4) prepared as in Examples 1 to 4 was dispersed in glyceryl monostearate (2 g), stearyl alcohol (4 g), octyldodecanol (2 g), and polyoxyethylene sorbitan monooleate (5 g) under heat. A solution prepared by dissolving methyl parahydroxybenzoate (0.1 g) and glycerol (5 g) in purified water (60 g) under heat was added thereto. The resulting mixture was emulsified by high-speed stirring and cooled to form a cream.

INDUSTRIAL APPLICABILITY

The transition metal phosphine complex of the present invention has excellent anticancer activity and low toxicity and is thus useful for an anticancer agent. The transition metal phosphine complex of the present invention has high water solubility. In the case where the complex is used as an anticancer agent, any of administration routes and formulations may be used. The agent acts effectively on an affected area at low doses. Low doses reduce side effects. Furthermore, according to the production method of the present invention, the transition metal phosphine complex may be produced by an industrially advantageous method.

The invention claimed is:

1. A transition metal phosphine complex compound represented by general formula (1):

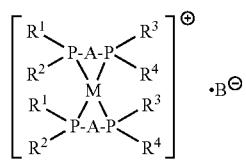

(1)

(wherein $R^1$s and $R^3$s each represent an alkyl group, a cycloalkyl group, an aryl group, an aralkyl group, a pyridyl group, or a pyrimidyl group; $R^2$s and $R^4$s each represent an alkyl group or a cycloalkyl group, provided that each $R^1$ and each $R^2$ are not the same group and that each $R^3$ and each $R^4$ are not the same group; As each represent a linear alkylene group or a cis-vinylene group; M represents a gold atom, a silver atom, a copper atom, or a platinum atom; and B represents an anionic species).

2. The transition metal phosphine complex compound according to claim 1, wherein $R^1$s and $R^3$s each represent a pyridyl group or a pyrimidyl group.

3. The transition metal phosphine complex compound according to claim 1 or 2, wherein M represents a gold atom.

4. The transition metal phosphine complex compound according to claim 1 or 2, wherein the transition metal phosphine complex is bis(1,2-bis(tert-butyl(2-pyridyl)phosphino)ethane)gold(I) chloride, bis(1,2-bis(tert-butyl(2-pyrimidyl)phosphino)ethane)gold(I) chloride, bis(1,2-bis(tert-butyl(methyl)phosphino)ethane)gold(I) chloride, bis(1,2-bis(methyl(phenyl)phosphino)ethane)gold(I) chloride, bis(1,2-bis(tert-butyl(2-pyridyl)phosphino)ethane)gold(I) bromide, bis(1,2-bis(tert-butyl(2-pyrimidyl)phosphino)ethane)gold(I) bromide, bis(1,2-bis(tert-butyl(methyl)phosphino)ethane)gold(I) bromide, bis(1,2-bis(methyl(phenyl)phosphino)ethane)gold(I) bromide, bis(1,2-bis(tert-butyl(2-pyridyl)phosphino)ethane)gold(I) iodide, bis(1,2-bis(tert-butyl(2-pyrimidyl)phosphino)ethane)gold(I) iodide, bis(1,2-bis(tert-butyl(methyl)phosphino)ethane)gold(I) iodide, or bis(1,2-bis(methyl(phenyl)phosphino)ethane)gold(1) iodide.

5. An optically active form of the transition metal phosphine complex compound according to claim 1 or 2.

6. A method for producing a transition metal phosphine complex compound, comprising:
providing a bisphosphine derivative represented by general formula (2):

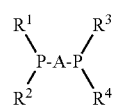

(2)

(wherein $R^1$ to $R^4$ and A have the same meanings as defined above);
reacting the bisphosphine derivative with a transition metal salt of gold, copper, platinum, or silver to produce a transition metal phosphine complex represented by general formula (1):

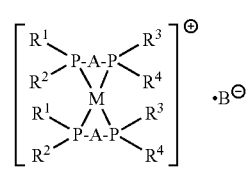

(1)

(wherein $R^1$s and $R^3$s each represent an alkyl group, a cycloalkyl group, an aryl group, an aralkyl group, a pyridyl group, or a pyrimidyl group; $R^2$s and $R^4$s each represent an alkyl group or a cycloalkyl group, provided that each $R^1$ and each $R^2$ are not the same group and that each $R^3$ and each $R^4$ are not the same group; As each represent a linear alkylene group or a cis-vinylene group; M represents a gold atom, a silver atom, a copper atom, or a platinum atom; and B represents an anionic species.

* * * * *